July 18, 1972 D. J. WALKER ET AL Plant Pat. 3,238
GLADIOLUS
Filed Dec. 29, 1970
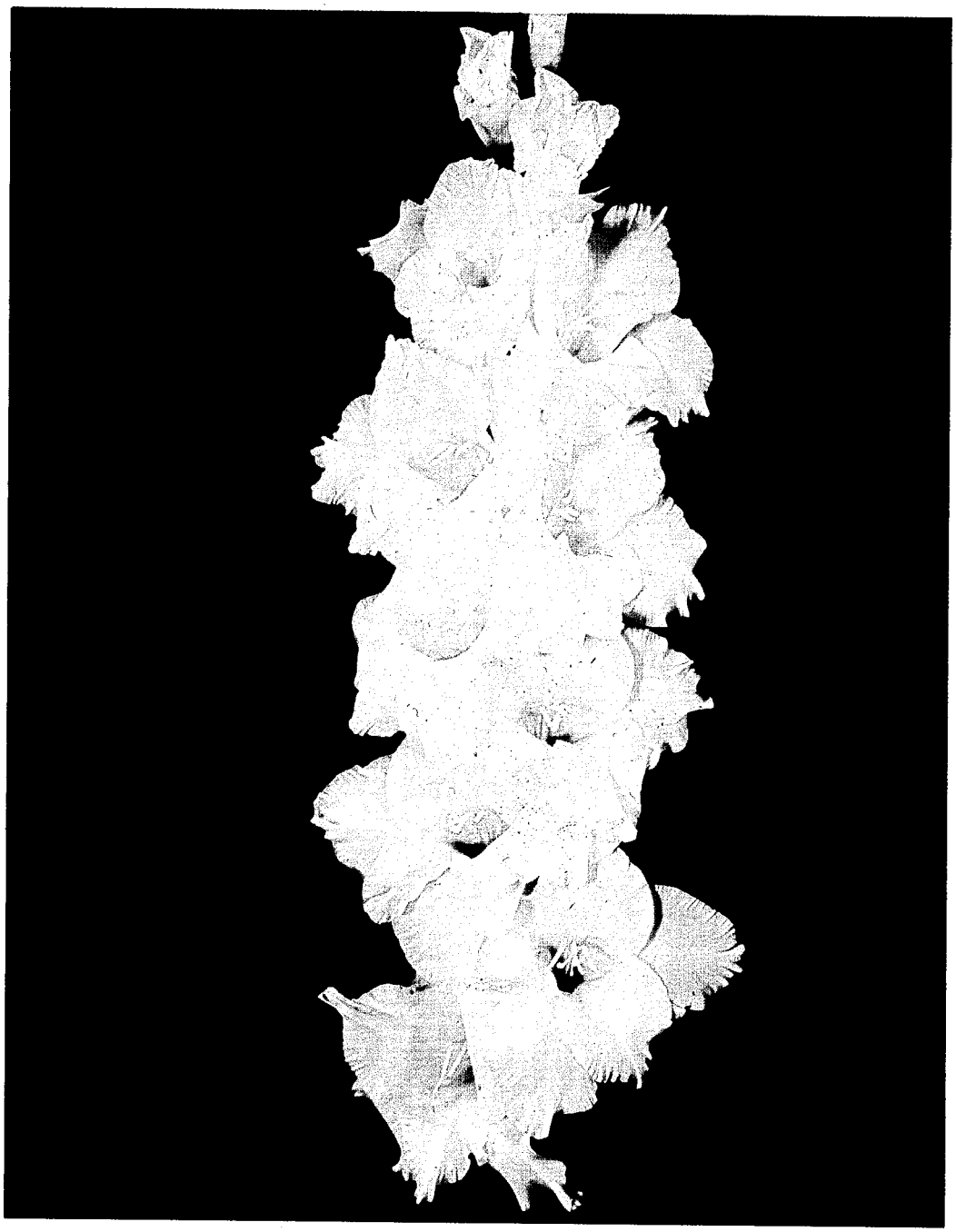

United States Patent Office

Plant Pat. 3,238
Patented July 18, 1972

3,238
GLADIOLUS

Donald J. Walker and Audrey I. Walker, New Hope, Pa., assignors to Selected Glads, Inc., New Albany, Ind.

Filed Dec. 29, 1970, Ser. No. 102,568
Int. Cl. A01h *5/00*
U.S. Cl. Plt.—85 1 Claim

This invention relates to a new and distinct variety of gladiolus plant.

This new gladiolus plant was originated by us by crossing the variety known as "Snow Velvet" with the variety known as "Alaska," "Snow Velvet" being the seed parent, "Alaska" being the pollen parent, both being unpatented but registered with the North America Gladiolus Registry, published in Sardina, N.Y.

The improved variety resulting from this breeding is evidenced by the following unique combination of characteristics which are outstanding therein and which distinguish our new variety from its parents, as well as from other varieties of which we are aware.

First: Pure glistening white color with no visible foreign color whatsoever; and even the stamens are white.

Second: The ability to open after shipping dry.

In addition to these major characteristics our variety is also endowed with the following characteristics:

(1) Good bud count;
(2) Stem freedom from crooking;
(3) Unusually long flowerhead;
(4) Good health;
(5) Admirable and consistent growth habits;
(6) Excellent propagative powers; and
(7) Modern ruffling.

We have asexually reproduced the new variety by cormels through several generations in Pennsylvania, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The colors depicted are as nearly true as is possible to achieve photographically.

The following is a detailed description of our new variety, with color terminology in accordance with the Horticultural Colour Charts issued by the British Colour Council and the Royal Horticultural Society, except where general color terms of ordinary dictionary significance are obvious.

PLANT

Growth: Vigorous and consistent; excellent propagator.

Blooming habit: Comes into bloom early; under normal conditions the first bloom appears approximately 72 days, in northern latitudes of the United States, after planting.

Stems:

*Form.*—Exceptionally tall and straight.
*Diameter at base.*—About ½ inch.
*Color at base.*—Approximately the same as leaves—Sheeles Green Plate 860/2.

Foliage: The corms of this new variety regularly produce at least seven leaves. They are Sheeles Green #860/2 in color. The leaves of this variety have no chlorophyll deficiency but are of a lighter green shade than most varieties. The average leaf is one and three-quarter inches wide at the base, grows thirty-six inches long, tapers gracefully to a point and droops artistically from the spot where the taper begins, about thirty inches from the ground.

Disease resistance: The variety has been found to be unusually resistant to the usual gladiolus plant diseases of a bacterial, viral or fungoid genesis.

Corms: Mature corms are plump and high-crowned with paper-like husks which are straw colored at the point of their attachment, continuing light straw colored to near the top where they are striped light garnet brown—Plate 918/4.

*Color of flesh.*—Barium yellow—Plate 503.

FLOWER

Spike:

*Form and size.*—Tall and straight with bloom spike 60 inches in height and regularly carrying 23 to 27 buds with flowerhead ranging about 30 inches long.

Bud:

*Size.*—About 3 to 3½ inches long when opening.
*Opening.*—On first blooming 3 or 4 buds open with 2 or 3 a day opening thereafter.

Flower:

*Arrangement.*—Flowerhead of the new variety has a formal placement wherein all florets face forward.
*Size.*—Individual florets average about 5 inches in diameter.
*Form.*—Florets are somewhat round, slightly recurved and quite ruffled.
*Keeping qualities.*—The flowers keep well.

Petals:

*Shape.*—Somewhat round and slightly recurved.
*Size.*—Upper petals—about 2 inches wide. Lip petals—about 1½ inches wide.
*Aspect.*—Substance is average. Surface is uneven and ruffled.
*Fragrance.*—None.
*Color.*—Pure glistening white—no available chart reference for this color.

REPRODUCTIVE ORGANS

Stamens:

*Color.*—Pure white.

Pistils:

*Color.*—Pure white.

GROWTH

Locality where grown and observed: New Hope, Pennsylvania.

Propagation: Holds its distinguishing characteristics through succeeding propagations from cormels.

It can be seen that this variety is unique in its color, and that even its reproductive organs and throat carry no other color. The variety is not inhibited white, but is cytogenetically termed recessive white.

What we claim is:

1. A new and distinct variety of gladiolus plant, substantially as herein shown and described, characterized particularly as to novelty by the unique combination of the pure glistening white color of its flower with no visible foreign color whatsoever, even in its stamens, and the ability to open after shipping dry.

No references cited.

ROBERT E. BAGWILL, Primary Examiner